United States Patent
Nowak

(10) Patent No.: US 12,161,515 B2
(45) Date of Patent: Dec. 10, 2024

(54) SURGICAL RETRACTOR SYSTEM AND MULTI-DIRECTIONAL JOINT CLAMP FOR SAME

(71) Applicant: Thompson Surgical Instruments, Inc., Traverse City, MI (US)

(72) Inventor: Steve Nowak, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 185 days.

(21) Appl. No.: 18/074,997

(22) Filed: Dec. 5, 2022

(65) Prior Publication Data

US 2023/0172685 A1 Jun. 8, 2023

Related U.S. Application Data

(62) Division of application No. 16/857,998, filed on Apr. 24, 2020, now Pat. No. 11,523,876.

(51) Int. Cl.
  *A61B 90/50* (2016.01)
  *A61B 17/02* (2006.01)
  *A61B 17/00* (2006.01)
  *A61B 90/57* (2016.01)

(52) U.S. Cl.
  CPC .......... *A61B 90/50* (2016.02); *A61B 17/0218* (2013.01); *A61B 2017/00367* (2013.01); *A61B 2017/00477* (2013.01); *A61B 2090/571* (2016.02)

(58) Field of Classification Search
  CPC ......... A61B 90/50; A61B 90/57; A61B 17/02; A61B 17/0218; A61B 17/00; F16B 2/18
  See application file for complete search history.

(56) References Cited

U.S. PATENT DOCUMENTS

| | | |
|---|---|---|
| 2,893,378 A | 7/1959 | Cooper |
| 3,221,743 A | 12/1965 | Thompson et al. |
| 3,965,890 A | 6/1976 | Gauthier |
| 4,421,108 A | 12/1983 | Cabrera et al. |
| 4,596,484 A | 6/1986 | Nakatani |
| 4,617,916 A | 10/1986 | LeVahn et al. |
| 4,813,401 A | 3/1989 | Grieshaber |
| 4,971,038 A | 11/1990 | Farley |
| 5,020,195 A | 6/1991 | LeVahn |
| 5,025,780 A | 6/1991 | Farley |
| 5,224,680 A | 7/1993 | Greenstein et al. |

(Continued)

OTHER PUBLICATIONS

International Search Report and Written Opinion for PCT/US2021/025880, mailed Jul. 8, 2021, 17 pages.

*Primary Examiner* — Christopher J Beccia
(74) *Attorney, Agent, or Firm* — McAndrews, Held & Malloy, Ltd.

(57) ABSTRACT

A joint clamp for a surgical retractor system includes clamps, a cam bolt, and a cam lever. The cam bolt passes through the clamps. A cam lever comprising a cam head pivotally attached an upper portion the cam bolt to permit rotation about a pivot axis that is perpendicular to a longitudinal axis of the cam bolt. The cam head includes an outer surface that results in a distance between the pivot axis and an upper surface of the clamps being greater when the cam lever is rotated about the pivot axis to a clamping position than when the cam lever is rotated about the pivot axis to a non-clamping position. The clamping force may be calibrated or set via a cam bolt having an adjustable length and/or via a setting screw.

20 Claims, 15 Drawing Sheets

(56) References Cited

U.S. PATENT DOCUMENTS

| | | |
|---|---|---|
| 5,515,744 A | 5/1996 | Liao |
| 5,609,565 A | 3/1997 | Nakamura |
| 5,792,046 A | 8/1998 | Dobrovolny |
| 5,846,192 A | 12/1998 | Teixido |
| 5,897,087 A | 4/1999 | Farley |
| 6,033,363 A | 3/2000 | Farley et al. |
| 6,302,843 B1 | 10/2001 | Lees et al. |
| 6,474,900 B2 | 11/2002 | Feng |
| 6,511,423 B2 | 1/2003 | Farley |
| 7,125,380 B2 | 10/2006 | Yager |
| 7,297,107 B1 | 11/2007 | Bjork et al. |
| 7,320,666 B2 | 1/2008 | Bjork et al. |
| 7,553,279 B1 | 6/2009 | Phillips et al. |
| 7,556,229 B2 | 7/2009 | Elliott et al. |
| 7,562,855 B2 | 7/2009 | Oetlinger |
| 7,758,502 B2 | 7/2010 | Phillips et al. |
| 9,089,299 B2 | 7/2015 | Nowak et al. |
| 9,636,785 B2 | 5/2017 | Traver et al. |
| 2006/0211920 A1 | 9/2006 | Bethke |
| 2008/0247818 A1 | 10/2008 | Oesch et al. |
| 2017/0042527 A1 | 2/2017 | Farley et al. |
| 2019/0209150 A1 | 7/2019 | Farley |

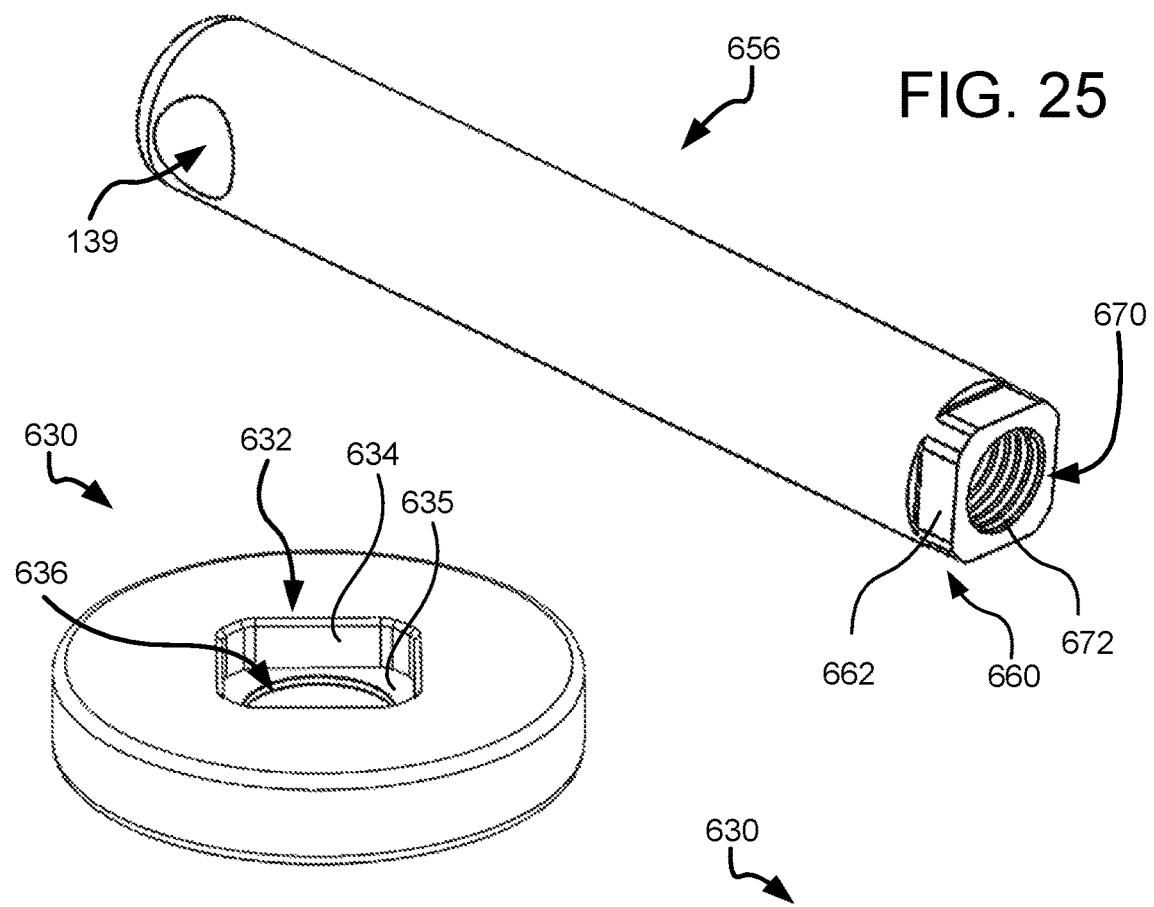
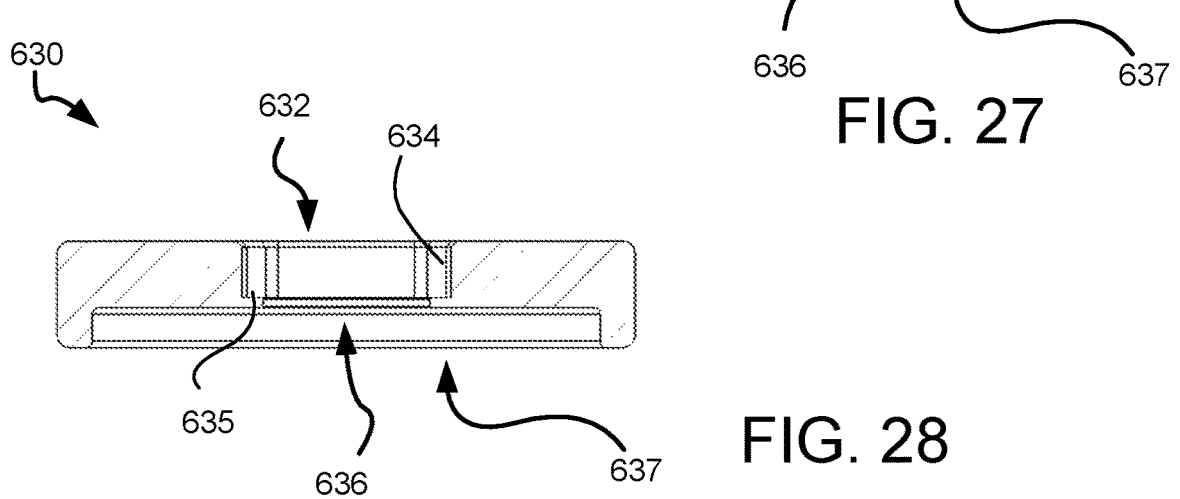

SURGICAL RETRACTOR SYSTEM AND MULTI-DIRECTIONAL JOINT CLAMP FOR SAME

BACKGROUND OF THE INVENTION

The present invention relates to retractor systems for use during surgical procedures.

During surgical procedures, a surgeon typically makes an incision in a patient to access a site of interest for the particular surgical procedure. To maintain clear access to the site of interest, a surgical retractor system is typically utilized. A surgical retractor system typically includes a rail clamp, a frame connected to the rail clamp by a joint clamp, and retractor blades that are connected to the frame by additional joint clamps. The rail clamp is commonly secured to an operating table and provides a fixed and sturdy support for the frame and the retractor blades. Each of the components in a typical surgical retractor system is conventionally made of stainless steel. Other materials such as aluminum and titanium have also been used.

Limitations and disadvantages of conventional and traditional approaches should become apparent to one of skill in the art, through comparison of such systems with aspects of the embodiments set forth in the remainder of the present disclosure.

BRIEF SUMMARY OF THE INVENTION

Surgical retractor systems and joint clamps for such surgical retractor systems are shown in and/or described in at least one figure of the present disclosure. Such surgical retractor systems, joint clamps, and/or other aspects of the present disclosure are set forth more completely in the claims. Advantages, aspects, novel features, as well as, details of illustrated embodiments will be more fully understood from the following description and figures.

BRIEF DESCRIPTION OF SEVERAL VIEWS OF THE DRAWINGS

FIG. 25 provides a perspective view of the cam bolt for the joint clamp of FIG. 24.

FIGS. 26 and 27 provide perspective views of a keyed washer for the joint clamp of FIG. 24.

FIG. 28 provides a cross-sectional view of the keyed washer shown in FIGS. 26 and 27.

DETAILED DESCRIPTION OF THE INVENTION

In the following detailed description, spatially orienting terms are used such as "left," "right," "vertical," "horizontal," and the like. It is to be understood that these terms are used for convenience of description of the illustrated embodiments in reference to the drawings. These terms do not necessarily describe the absolute location in space, such as left, right, upward, downward, etc., that any part must assume.

Figure 1:
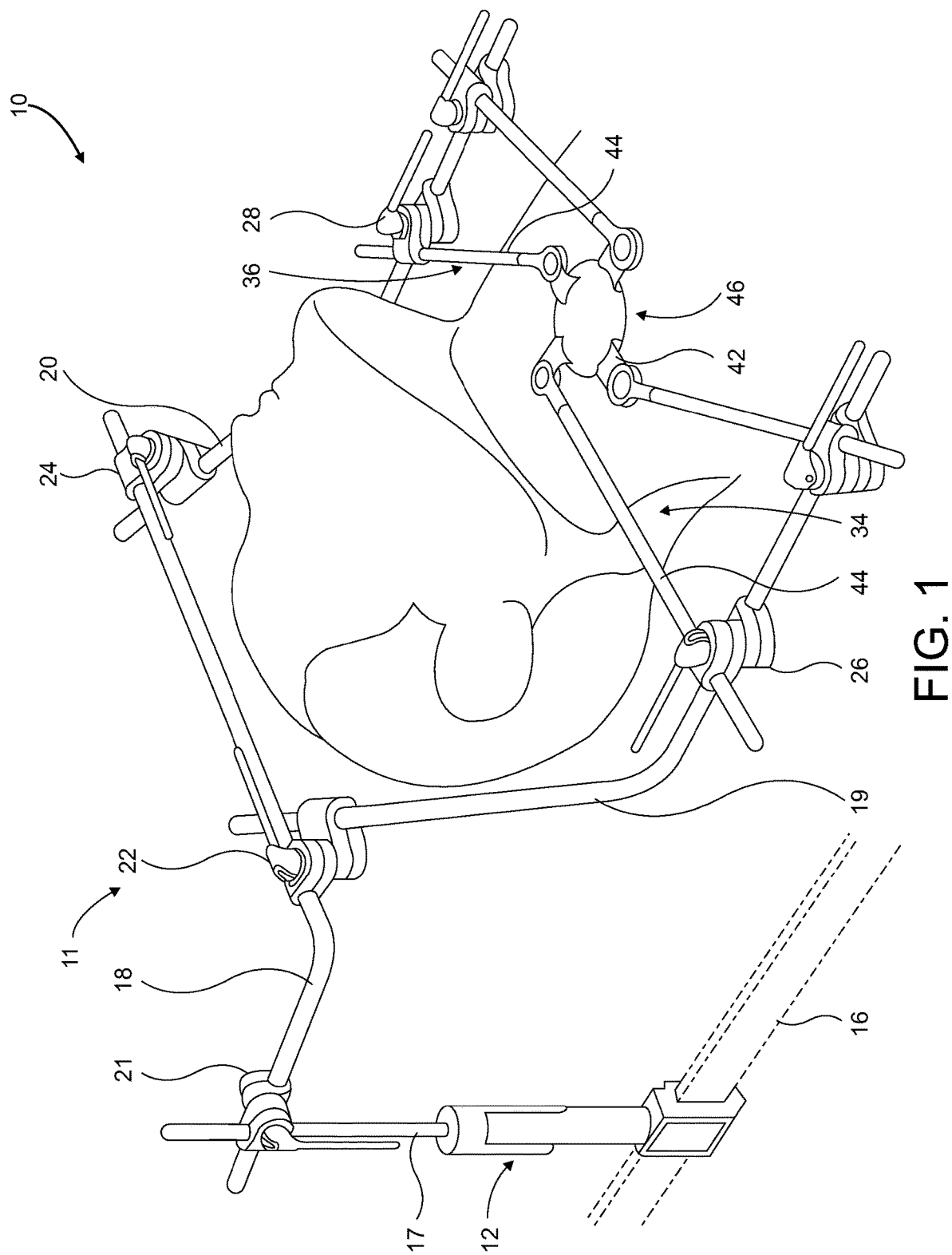
FIG. 1 is a perspective view of a surgical retractor system having joint clamps per one or more embodiments described herein.

As shown in FIG. 1, a surgical retraction system 10 includes a frame assembly 11. The frame assembly 11 may secure retractor blades 34, 36 to a surgical table 16 to eliminate unwanted relative movement between the retractor blades 34, 36 and the surgical table 16. To this end, the frame assembly 11 may include adjustable rail clamps 12, posts 17, cross bars 18, extension arms 19, 20, and multi-directional joint clamps 21, 22, 24, 26, 28 (hereafter "joint clamp or joint clamps"). A first adjustable rail clamp 12 may be secured to the surgical table 16. A second adjustable rail clamp (not shown) may be secured to the opposite side of the surgical table 16 for increased stability, if desired or needed. A post 17 may extend vertically from rail clamp 12 to provide support for a cross bar 18 which in turn provides support for a pair of extension arms 19, 20. Cross bar 18 may be secured to post 17 by a joint clamp 21. Extension arms 19, 20 may be respectively secured to cross bar 18 by a pair of joint clamps 22, 24. Extension arms 19, 20 may be secured directly to post 17 by a joint clamp, thus eliminating the need for cross bar 18 in certain circumstances.

Additional joint clamps 26, 28 may be disposed along extension arms 19, 20 and may rigidly secure retractor blades 34, 36 to extension arms 19, 20. Each retractor blade 34, 36 may include a blade portion 42 and a retractor arm 44. Blade portion 42 may extend downwardly into the incision 46 made by the surgeon and may retract anatomy to make the incision 46 accessible to the surgeon.

Figure 2:
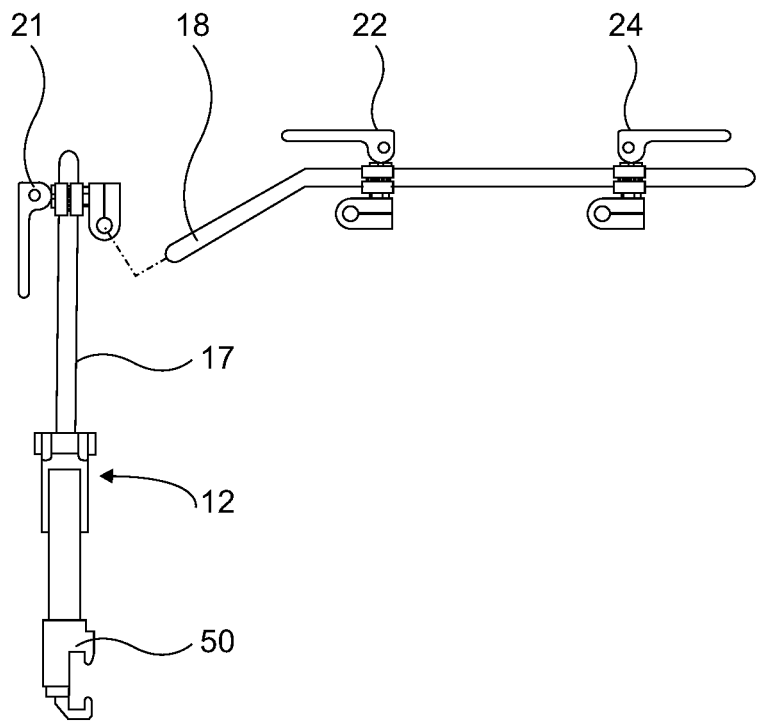
FIG. 2 is an elevated view of the rail clamp, joint clamps, and cross bar of the surgical retractor system shown in FIG. 1.
Figure 3:
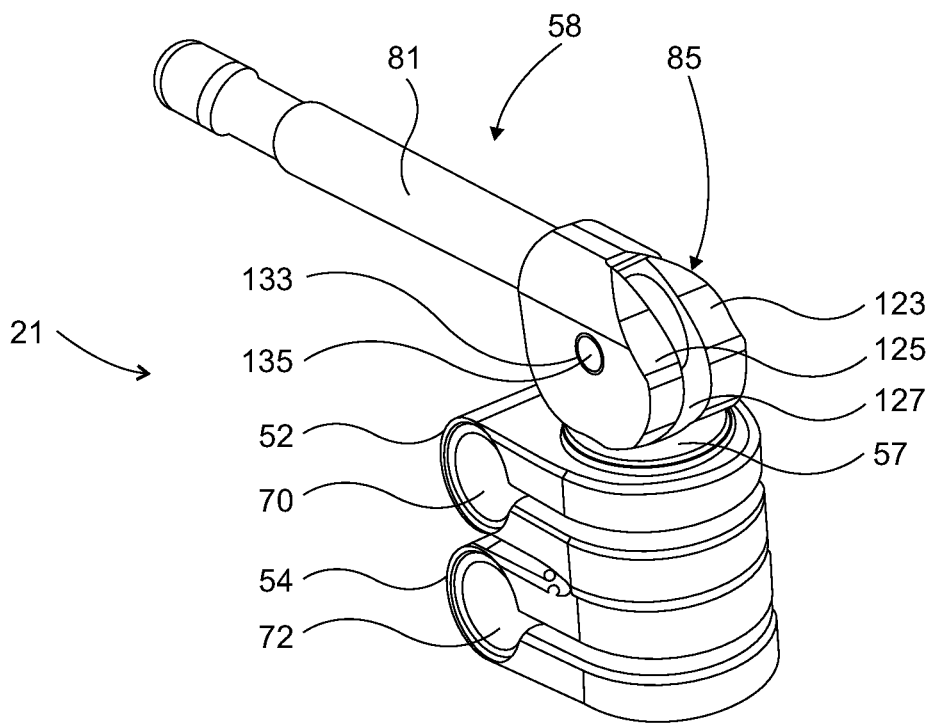
FIG. 3 is a perspective view of a joint clamp of the retractor system shown in FIG. 1.

FIG. 2 is an elevated view of the rail clamp 12 and cross bar 18. Of course, as noted above, extension arm 19 or 20 may be connected directly to adjustable rail clamp 12. The rail clamp includes a clamp 50 that may be secured to surgical table 16 (FIG. 1). This may be a conventional clamp as presently used in the industry and provides for a secure attachment of the adjustable rail clamp 12 to the surgical table 16. Joint clamp 21 is shown at the upper most extremity of post 17. This position of the joint clamp 21 enables the user to locate cross bar 18 at a height sufficient for the frame assembly 11 (FIG. 1) to be used during surgical procedures. FIG. 2 further shows joint clamps 22, 24 in their position on cross bar 18. Clamps 22 and 24 may be identical to each other or different depending on the intended use of each of those clamps. Additionally, these joint clamps 22, 24 may each be the same as or different to the joint clamp 21 on post 17.

Referring to FIGS. 3-5 and 14, joint clamp 21 includes a first clamp 52 and a second clamp 54. Joint clamp 21 includes a cam bolt 56 as well as a cam lever 58 for bringing first clamp 52 and second clamp 54 into a clamping position or into an unclamping position. Joint clamp 21 may also include a washer 57 positioned between the cam lever 58 and the first clamp 52.

The first clamp 52 may include a passage 70, which is intended to accommodate, for example, post 17 of rail clamp 12 (FIG. 2). Similarly, the second clamp 54 may include a passage 72. Passage 72 is intended to accommodate, for example, cross bar 18 (FIG. 2). This type of joint clamp is more fully described in U.S. Pat. Nos. 5,897,087 and 6,033,363, which are incorporated herein by reference.

The first cylindrical passage 70 of the first clamp 52 is defined by a broken cylindrical surface 71. The cylindrical surface 71 is broken along two parallel legs 73, 74 which run the axial length of the surface 71 to define a gap 75. Legs 73, 74 are movable with respect to one another in order to shorten the gap 75 and thus constrict the area circumscribed by cylindrical surface 71. Each leg 73, 74 defines a respective planar surface 76, 77. Each planar surface 76, 77 is generally parallel to the longitudinal axis of cylindrical passage 70. The application of a clamping forces directs forces against an upper surface 78a and a lower surface 78b of the first clamp 52 in a direction toward the gap 75 and parallel to the longitudinal axis of cam bolt 56 and serves to move planar surfaces 76, 77 toward each other, thus reducing a circumference or diameter of first cylindrical passage 70 and constricting the area within first cylindrical passage 70.

Similarly, the second cylindrical passage 72 of the second clamp 54 is defined by a broken cylindrical surface 80. The cylindrical surface 80 is broken along two parallel legs 82, 84 which run the axial length of the surface 80 to define a gap 86. Legs 82, 84 are movable with respect to one another in order to shorten the gap 86 and thus constrict the area circumscribed by cylindrical surface 80. Each leg 82, 84 defines a respective planar surface 90, 92. Each planar surface 90, 92 is generally parallel to the longitudinal axis of cylindrical passage 80. The application of a clamping force directs forces against an upper surface 94a and a lower surface 94b of the second clamp 54 in a direction toward the gap 86 and parallel to the longitudinal axis of cam bolt 56 and serves to move planar surfaces 90, 92 toward each other constricting the area within second cylindrical passage 72.

The clamps 52, 54 further include locking teeth. In particular, a first set of locking teeth 99b may be disposed on the lower surface 78b of first clamp 52 and a second set of locking teeth 99a may be disposed on the upper surface 94a of second clamp 54. The sets of locking teeth 99a, 99b engage each other when clamps 52, 54 are compressed together by cam lever 58, thereby fixing the positions of clamps 52, 54 relative to one another.

The cam lever 58 includes a cylindrical-shaped handle 81 having a distal end 83 connected to a cam head 85. Cam head 85 is pivotally mounted to cam bolt 56 such that rotation of the cam lever 58 about a pivot axis 88 selectively places first clamp 52 and second clamp 54 into clamping positions and unclamping positions. The cam bolt 56 may be cylindrical in cross section and may extend through the cylindrical apertures 112, 116 in clamps 52, 54.

Figure 4:
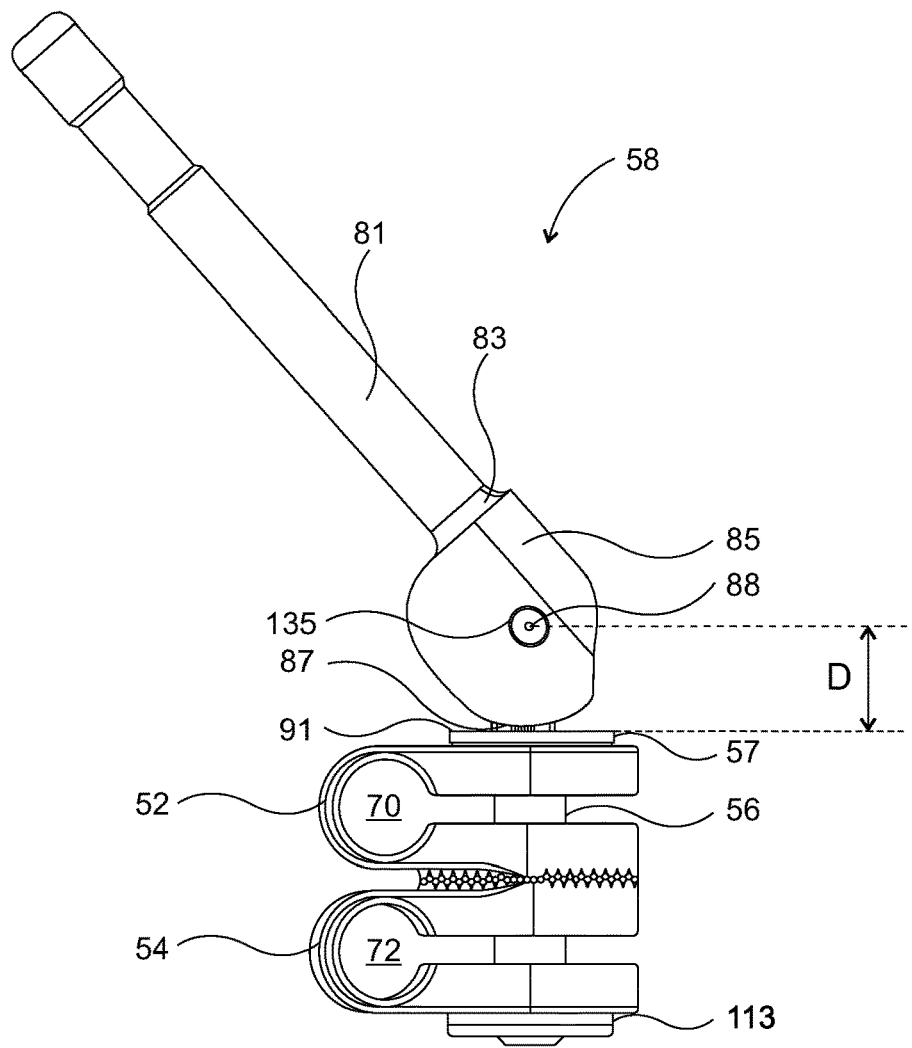
FIG. 4 is a side view of the joint clamp of FIG. 3 in an open or unclamped position.
Figure 5:
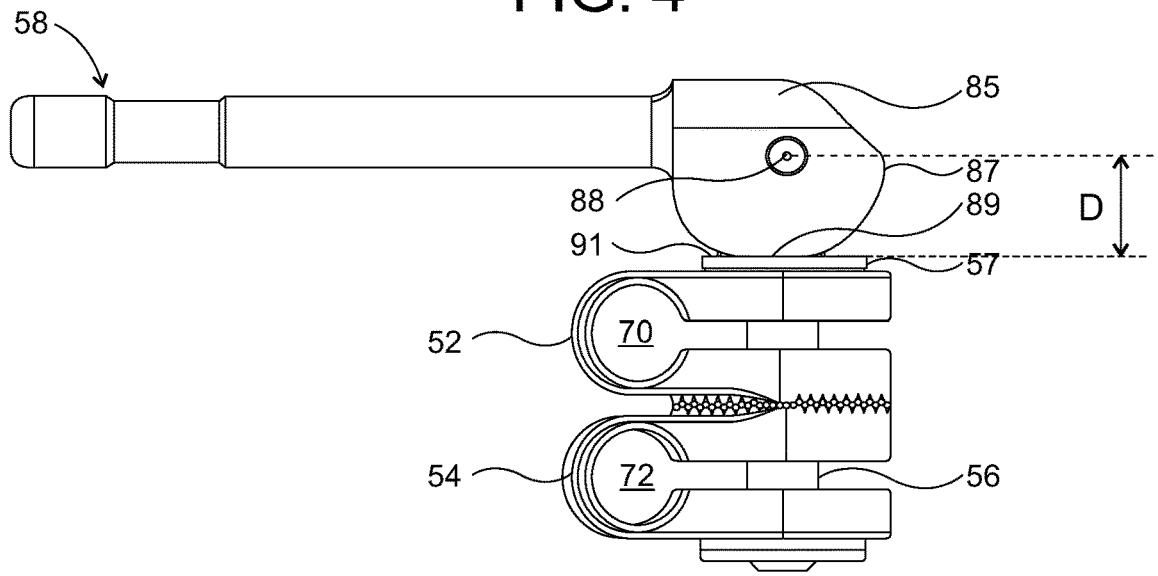
FIG. 5 is a side view of the joint clamp of FIG. 3 in a closed or clamping position.
Figure 6:
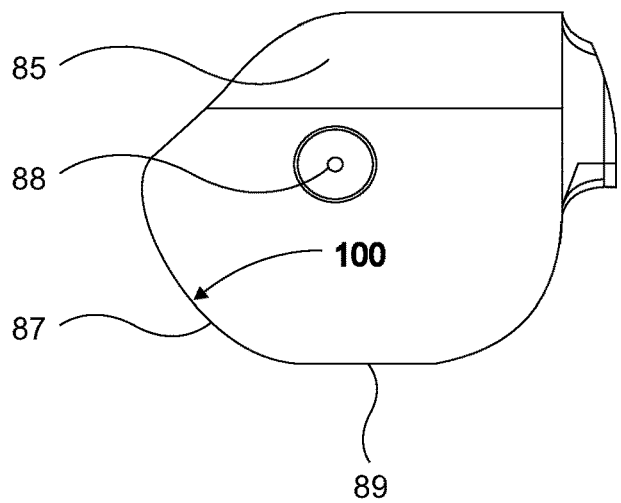
FIG. 6 is a side view of the cam head of the joint clamp shown in FIG. 3.

Referring now to FIG. 6, an outer edge 100 of the cam head 85 is eccentric or multi-curved, such that the distance D between the pivot axis 88 and the upper surface 91 of the washer 57 increases as the cam lever 58 is moved from its open position (e.g., FIG. 4) towards its closed position (e.g., FIG. 5). Hence, movement of cam lever 58 towards its closed position draws cam bolt 56 upwardly through cylindrical apertures 112, 116, compressing clamps 52, 54 between the outer edge 100 of the cam head 85 and a stop, such as the nut 113, secured to the distal end of cam bolt 56. Compression of the resilient clamps 52, 54 initially causes the sets of locking teeth 99a, 99b to engage each other, thereby fixing the positions of the clamps 52, 54 relative to each other. Further compression of clamps 52, 54 constricts the area circumscribed by cylindrical passages 70, 72 to secure clamps 52, 54 to the arms passing through cylindrical passages 70, 72.

Rotation of cam lever 58 towards its open position moves cam bolt 56 downwardly through cylindrical apertures 112, 116. Due to the downward movement of cam bolt 56, the nut 113 may be urged away from aperture 116, thus reducing or removing a clamping force applied to resilient clamps 52, 53. At the open position, clamps 52, 54 are loosely held on cam bolt 56, and may be rotated relative to one another about cam bolt 56. The nut 113 may prevent clamps 52, 54 from being removed for the cam bolt 56. The removed or reduced compression on clamps 52, 54 may cause cylindrical passages 70, 72 to expand their diameter, allowing clamps 52, 54 to be moved relative to posts positioned in cylindrical passages 70, 72. The open position may also allow the various clamp components to be accessed for cleaning.

FIG. 4 shows the two clamps 52, 54 in their unclamped positions. Cam lever 58 is rotated upwardly to an open position for releasing or untightening of clamps 52, 54. In this open position, a release surface 87 of cam head 85 is moved or rotated to a position above washer 57 providing little or no contact between cam head 85 and washer 57 and reducing the distance D between the pivot axis 88 and the upper surface 91 of the washer 57. This removes the force on clamps 52, 54 allowing them to expand and open their respective passages 70, 72 to a full extent.

FIG. 5 shows the two clamps 52, 54 in their clamped positions. Cam lever 58 is rotated downwardly to a closed position for tightening of clamp 52, 54. In this closed position, release surface 87 is rotated away from washer 57 and a flat planar surface 89 of cam head 85 engages washer 57. To enter this closed position, a clamping force is applied to clamps 52, 54 which constricts passages 70, 72.

Planar surface 89 serves to lock handle 81 into position. Because surface 89 is a flat planar surface and contacts the flat planar top surface 91 of the washer 57, the reverse movement of cam lever 58 into an open position requires more force making it difficult for cam head 85 to unintentionally loosen and rotate away from its closed position of FIG. 5.

FIG. 6 is a side view of cam head 85 illustrating the surfaces 87, 89. Surfaces 87, 89 extend across the bottom of cam head 85. Surfaces 87, 89 are positioned on the cam head relative to axis 88 so as to engage the flat top surface 91 (FIG. 5) of washer 57 when the cam lever 58 is pivoted.

Referring to FIGS. 7A-7C and FIG. 8, washer 57 is generally cylindrical in shape, and has a cone-like configured shape at its bottom. Washer 57 includes an outer cylindrical surface 101 and a truncated-cone surface 103. An aperture 105 extends fully through the washer 57 terminating at the end of conical surface 103. Aperture 105 has a diameter to receive cam bolt 56 (FIG. 4) which is cylindrical in shape.

Figure 10:
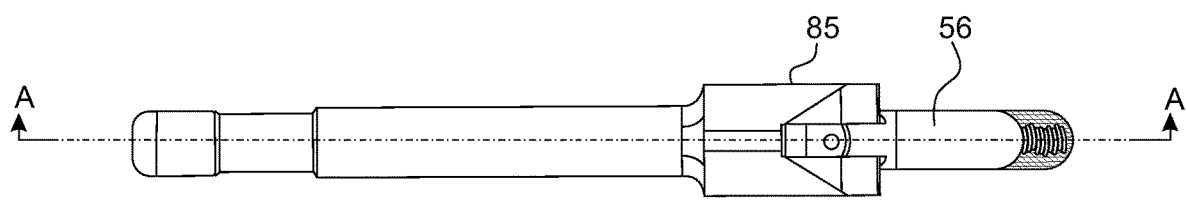
FIG. 10 is a top view of the joint clamp shown in FIG. 3.
Figure 11:
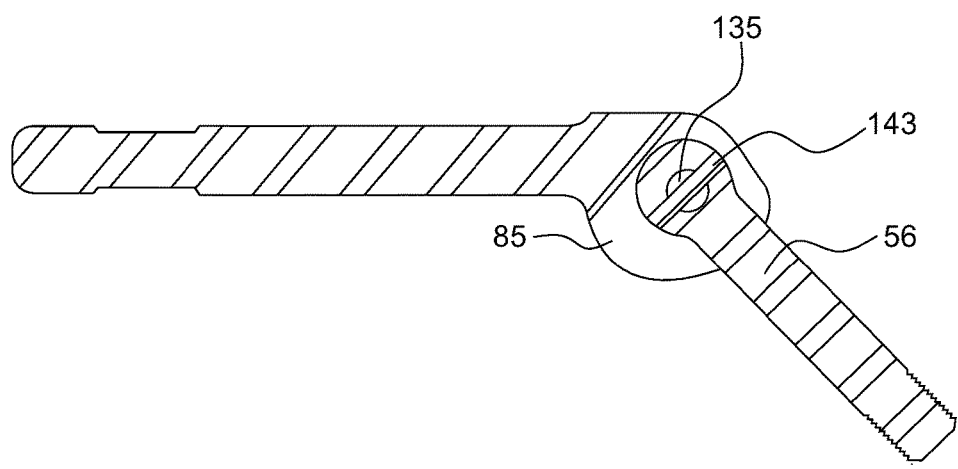
FIG. 11 is a cross sectional side view of the joint clamp shown in FIG. 9 along lines A-A.

Referring to FIGS. 4, 10 and 11, cam bolt 56 extends into cam head 85 and is rotatably secured in place by a cam pivot pin 135. This allows pivoting of cam lever 58 into its open position (FIG. 4) and into its closed position (FIG. 5).

Figure 7A:
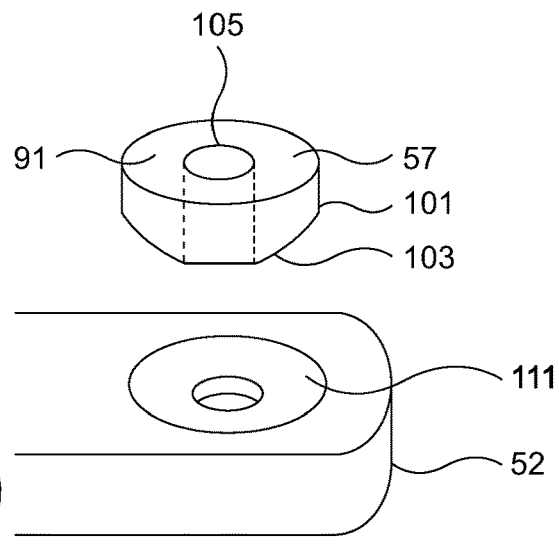
FIGS. 7A-7C depicts aspects of a washer and its interaction with a clamp of the joint clamp shown in FIG. 3.
Figure 7B:
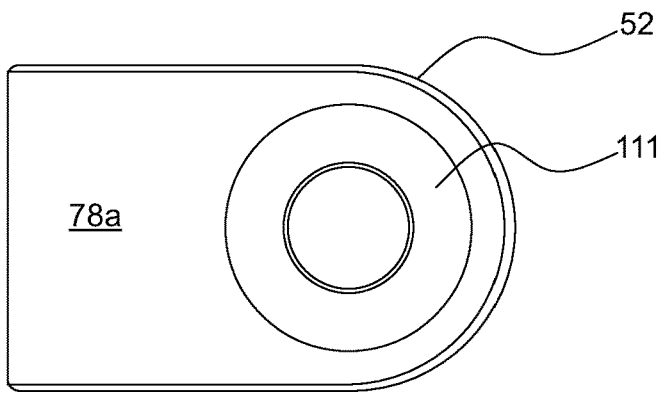
Figure 7C:
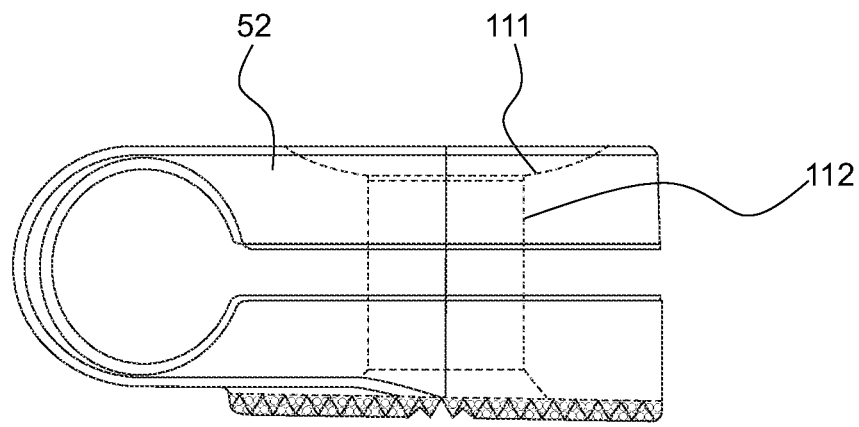
Figure 8:
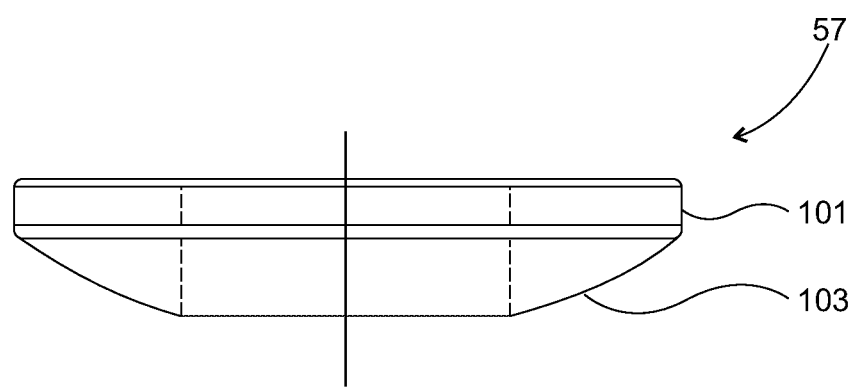
FIG. 8 is a side view of the washer shown in FIG. 7A.
Figure 14:
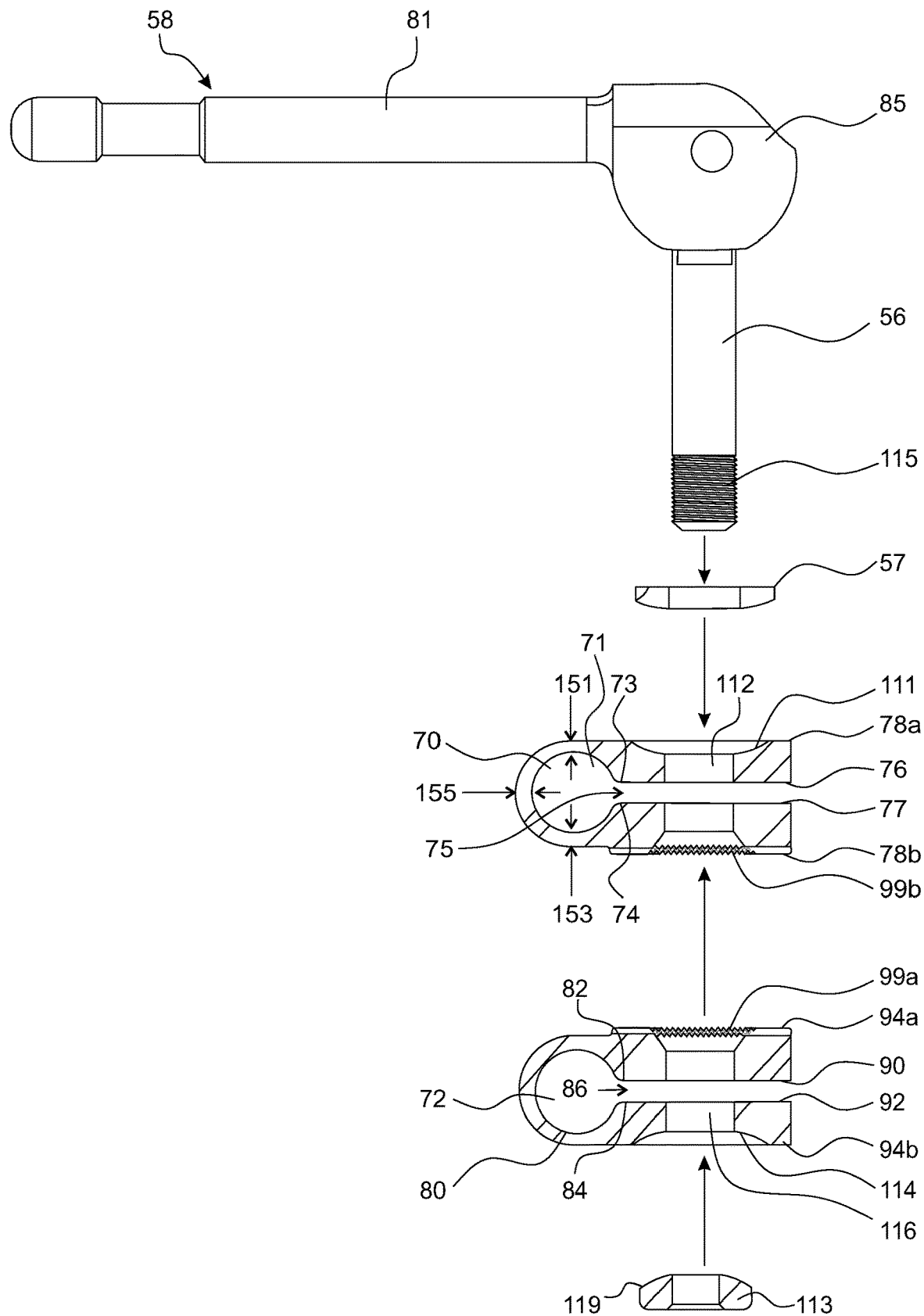
FIG. 14 is an exploded view of some components of the joint clamp shown in FIG. 3

Referring again to FIGS. 7A-7C, clamp 52 has a conically shaped aperture 111 to receive and mate with the conical surface 103 of washer 57. As shown in FIG. 7C, conical aperture 111 meets with cylindrical aperture 112 which has a diameter to receive cam bolt 56. Similarly, clamp 54 has a conically shaped aperture 114 to receive and mate with the conical surface 119 of nut 113. See, FIG. 14. As shown in FIG. 14, conical aperture 114 meets with cylindrical aperture 116 which has a diameter to receive cam bolt 56.

Figure 9:
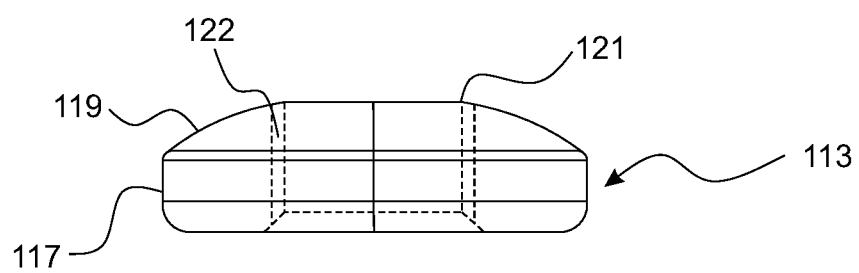
FIG. 9 is a side view of a nut of the joint clamp shown in FIG. 3.
Figure 12:
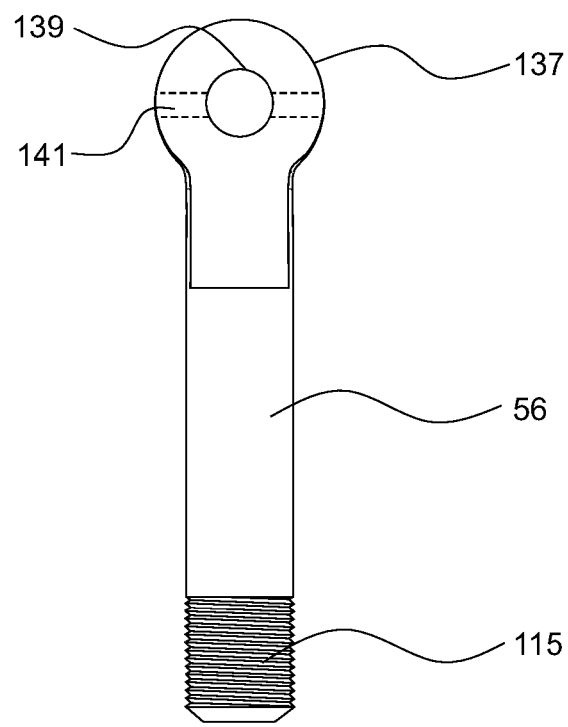
FIG. 12 is a side view of a cam bolt of the joint clamp shown in FIG. 3.

As shown in FIG. 4, a nut 113 is threaded onto the distal end of cam bolt 56. Threads 115 are shown in FIG. 12. Referring to FIG. 9, nut 113 is generally cylindrical in shape and has a cone-like configured shape at its top. Nut 113 includes a cylindrical surface 117 and a truncated-cone surface 119. An aperture 121 extends fully through nut 113 terminating at the end of conical surface 119. Aperture 121 has a diameter to receive cam bolt 56 and has threads 122 to mate with threads 115 on cam bolt 56 (FIG. 12).

The nut 113 may be welded to the cam bolt 56 after being threaded to the distal end of the cam bolt 56. Such welding may prevent further rotation of the nut 113 in relation to the cam bolt 56 about a longitudinal axis of the cam bolt 56, but may permit rotation of the nut 113 with respect the clamps 52, 54 about the longitudinal axis of the cam bolt 56. Because nut 113 is rounded, the cam bolt 56 with welded nut 113 may be rotated 360°, even when nut 113 is partially drawn into aperture 116. This may permit the surgeon to rotate handle 81 to a convenient position, even after clamps 52, 54 have been compressed.

Prior to welding, the nut 113 may be rotated in one direction (e.g., clockwise) to tighten the nut 113 and increase a clamping force applied by the clamps 52, 54 and may be rotated in the opposite direction (e.g. counter-clockwise) to loosen the nut 113 and decrease the clamping force applied by the clamps 52, 54. In this manner, the clamping force of the clamps 52, 54 may be calibrated to a desired force. After obtaining the desired, calibrated clamping force, the nut 113 may be welded to ensure the nut 113 does not rotate further and the desired, clamping force is maintained.

Referring again to FIG. 3, cam head 85 is shaped to include two extending side members 123, 125 forming an interposed channel 127. Channel 127 is defined by two planar side surfaces 129, 131 (FIG. 13) of the side members 123, 125. Each side member includes a cylindrical aperture 133 (FIG. 3) which are aligned along their axis. A cam pin 135 (FIG. 3) passes through cylindrical apertures 133. Cam pin 135 is held fixed relative to cam head 85.

Figure 13:
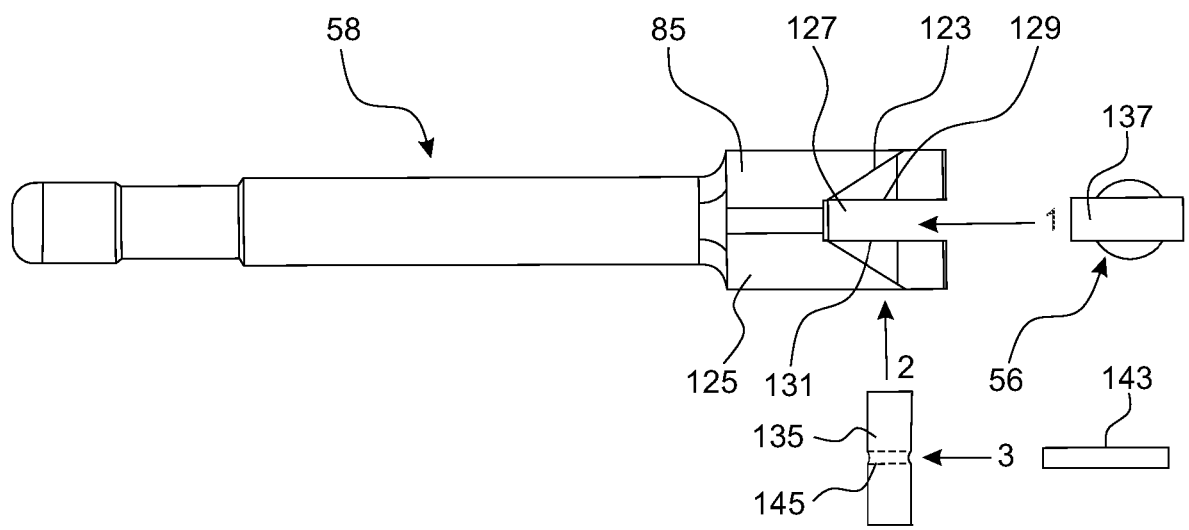
FIG. 13 is an exploded view of some components of the joint clamp shown in FIG. 3

As shown in FIG. 12, a top end 137 of the cam bolt 56 is generally planar in shape as best seen in FIG. 13, for movement within channel 127. Top end 137 (FIG. 12) includes a cylindrical aperture 139 for receiving cam pin 135 (FIG. 11) of cam head 85. Top end 137 rotates about cam pin 135. FIGS. 10 and 11 illustrate the cam bolt 56 being rotatably connected to cam pin 135.

As shown in FIG. 12, cam bolt 56 includes an additional cylindrical aperture 141 which passes through top end 137. Aperture 141 is located orthogonal to aperture 139, and aperture 141 is positioned to intersect with aperture 139, as shown in FIG. 12. Aperture 141 is sized to receive a lock pin 143, as shown in FIG. 11.

Referring to FIG. 13, the lever 58 is assembled, by initially positioning the top end 137 of cam bolt 56 into channel 127 of cam head 85. Cam pin 135 is next passed through apertures 133 (FIG. 3) in each of side members 123, 125 of the cam head and into aperture 139 (FIG. 12) of the cam bolt head. Finally, lock pin 143 (FIG. 13) is passed through aperture 141 (FIG. 12) located in the top end of cam bolt 56 and is passed through an aperture 145 in cam pin 135.

Thus, cam bolt 56 is held in position by both the aperture 139 in the cam bolt as well as the lock pin 143. Lock pin 143 secures the cam bolt 56 to the cam pin 135, and thus increases the wear surface between cam bolt 56 and the cam head 85.

Referring to FIG. 14, passages 70, 72 of the two clamps 52, 54 are shaped in an offset manner. Particularly, the wall thickness at 151 above each of passages 70, 72 and the wall thickness at 153 below each of passages 70, 72 is set at 0.070 inches. Whereas, the wall thickness at 155 between the hole and the distal end of the respective clamps is 0.100 inches. This, slight offset of the hole position serves to prevent the collapse of the hole due to continued use of the clamp without rods located in the passages 70, 72, e.g., without a retractor arm 44 (FIG. 1) or extension arms 19, 20 or cross bar 18 or post 17, within passages 70, 72.

Figure 15:
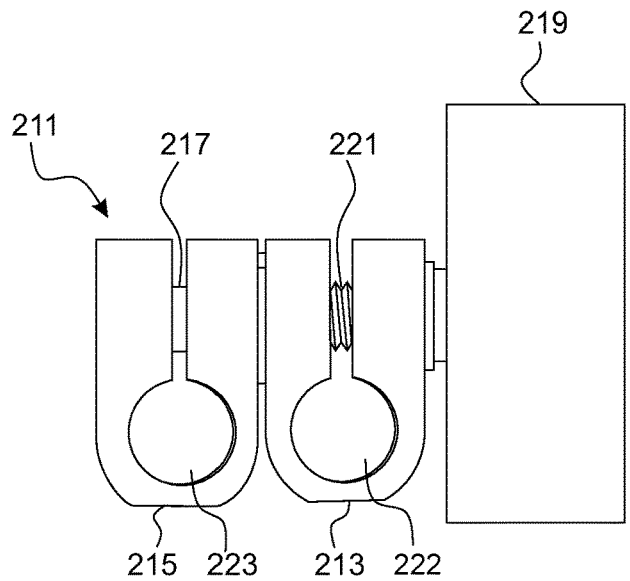
FIG. 15 is a side view of a second embodiment of a joint clamp.

A second embodiment of a joint clamp is shown in FIG. 15. In particular, the joint clamp 211 includes a first clamp 213 and a second clamp 215. Joint clamp 211 includes a bolt 217 as well as a turn-handle 219 for bringing first clamp 213 and second clamp 215 into a clamping position or into an unclamping position. Bolt 217 includes a threaded portion 221 that mates with a second threaded portion (not shown) formed in the turn-handle 219. As the turn-handle 219 is rotated, bolt 217 is drawn upwardly into the turn-handle 219 moving the two clamps 213, 215 together in order to perform the clamping function.

First clamp 213 includes a passage 222 which is intended to accommodate, for example, post 17 of rail clamp 12 (FIG. 2). Similarly, second clamp 215 includes a passage 223. Passage 223 is intended to accommodate, for example, cross bar 18 (FIG. 2). Passages 222, 223 may be shaped in an offset manner similar to passages 70, 72 as described above in relation to FIG. 14.

Figure 16:
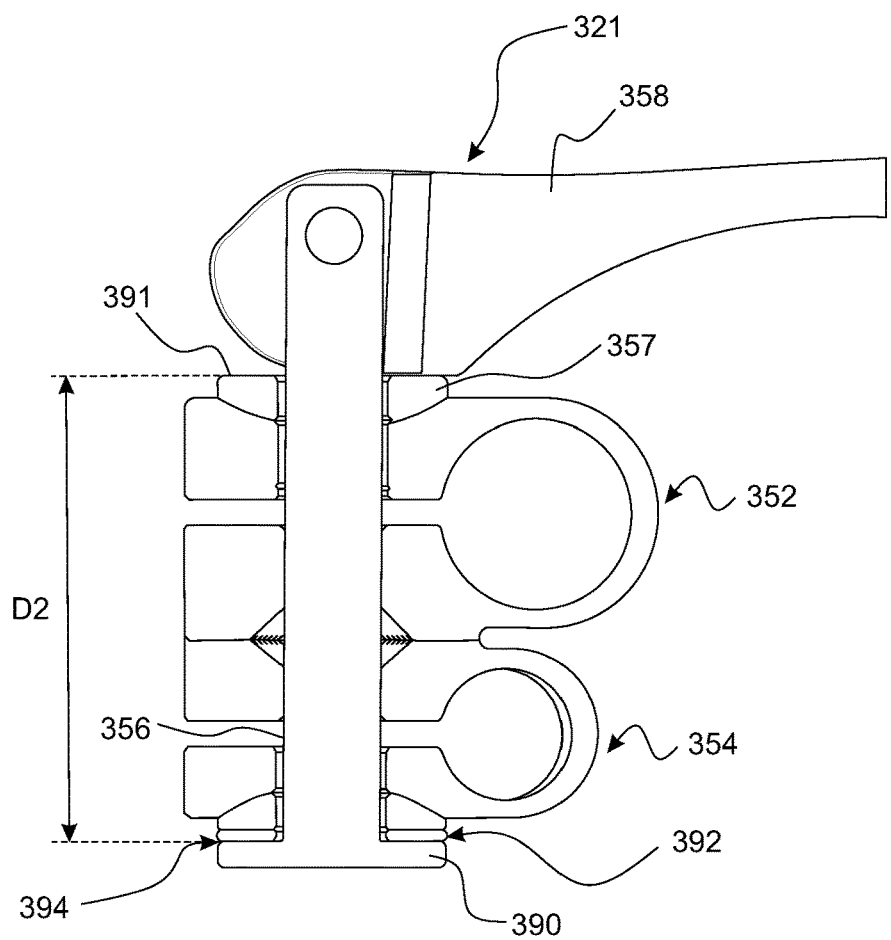
FIG. 16 is a side view of a third embodiment of a joint clamp.

A third embodiment of a joint clamp is shown in FIG. 16. The joint clamp 321 of FIG. 16 may be implemented in a manner similar to the multi-directional joint clamp 21 of FIGS. 3-14. However, the joint clamp 321 uses a different type of stop for the cam bolt. In particular, the joint clamp 321 may include a cam bolt 356 with an integral or fixed head 390 at its distal end instead of a nut. The head 390 may engage a shim 392, which may adjust a distance D2 between a top surface 391 of the washer 357 and a top surface 394 of the integral head 390. A thicker shim 392 increases the distance D2 and thereby increases the pressure load placed on the clamps 352, 354 by the cam lever 358 when in a clamping position since the length of the cam bolt 356 remains unchanged. Conversely, a thinner shim 392 decreases the distance D2 and thereby decreases the pressure load placed on the clamps 352, 354. Thus, a desired pressure load may be obtained by selecting a shim 392 having an appropriate thickness. The joint clamp 21 of FIGS. 3-14 may also adjust a pressure load applied by its cam lever 58. However, the joint clamp 21 may achieve such result by tightening or loosening the nut 113 instead of or in addition to using a shim 392.

Figure 17:
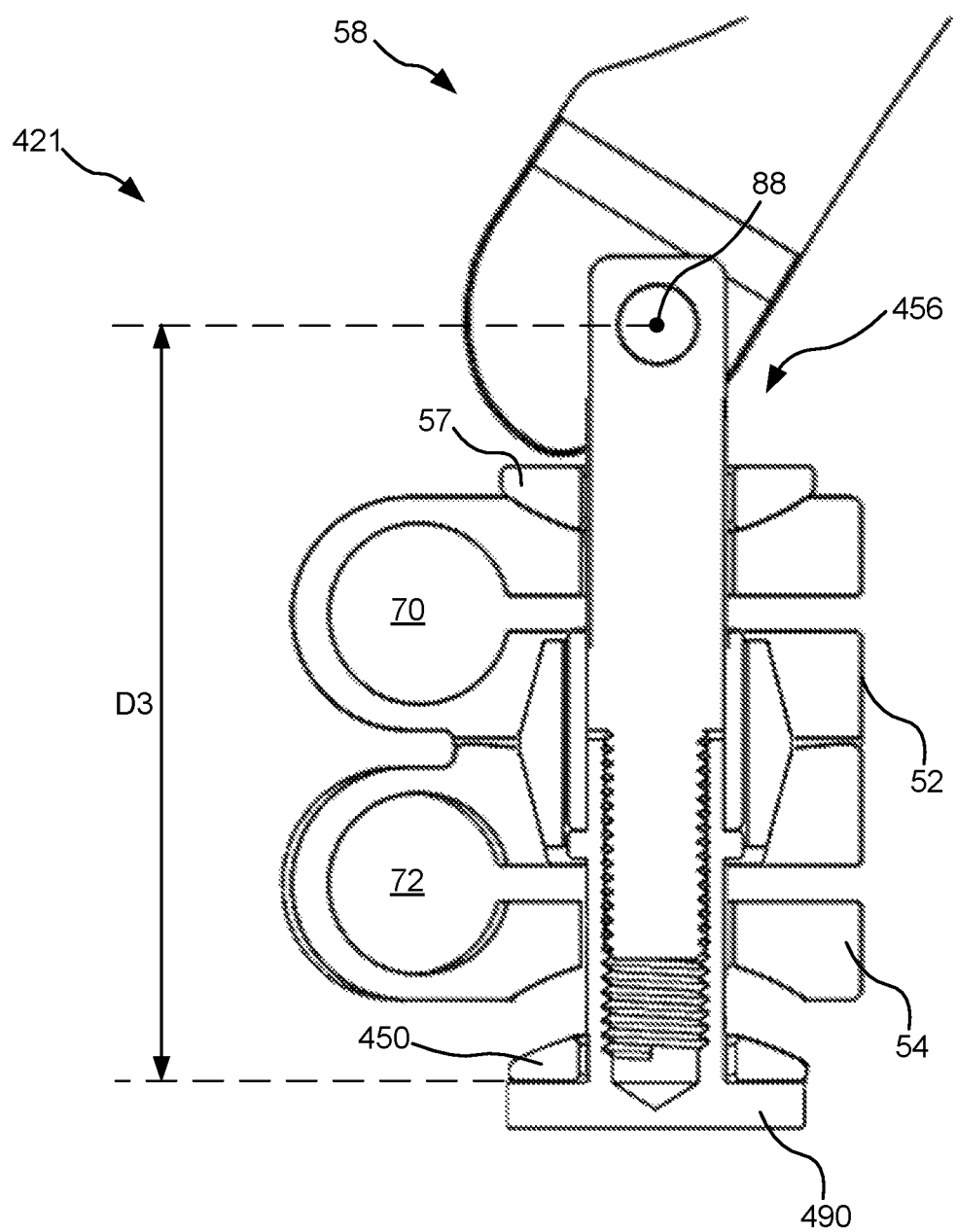
FIG. 17 shows a fourth embodiment of a joint clamp.
Figure 18:
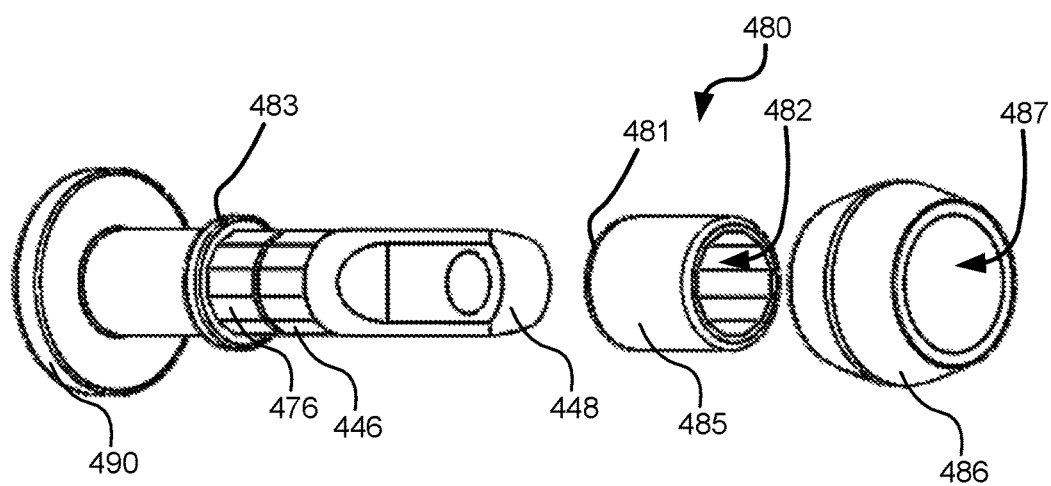
FIG. 18 provides a perspective view of the cam bolt, sleeve, and bushing of the joint clamp shown in FIG. 17.
Figure 19:
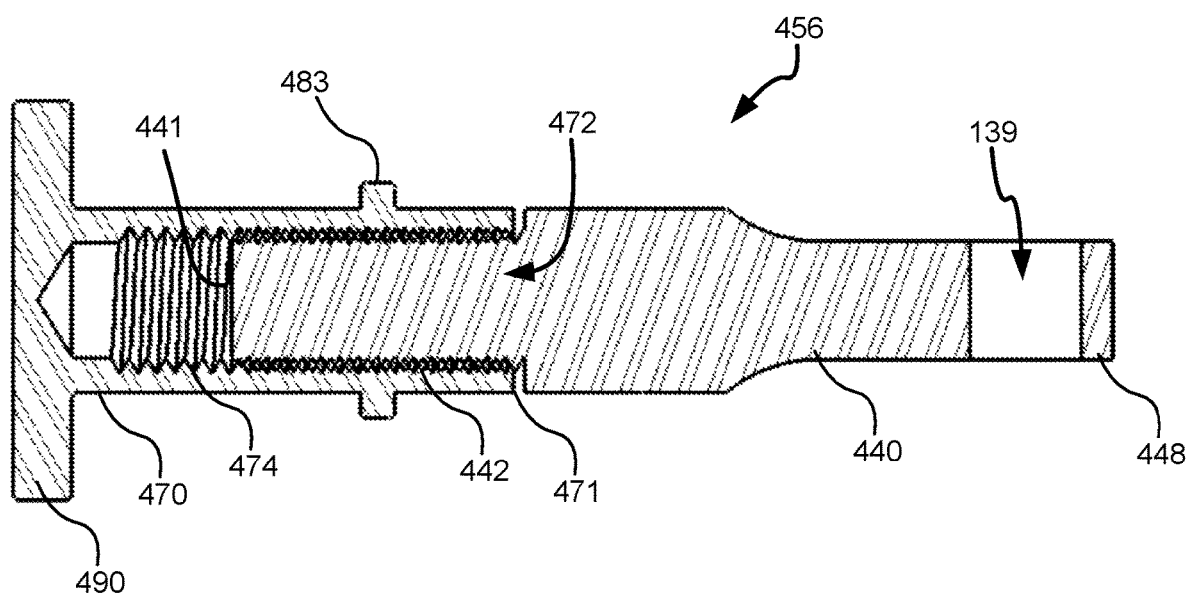
FIG. 19 provides a cross-sectional view of the cam bolt of FIG. 18.
Figure 20:
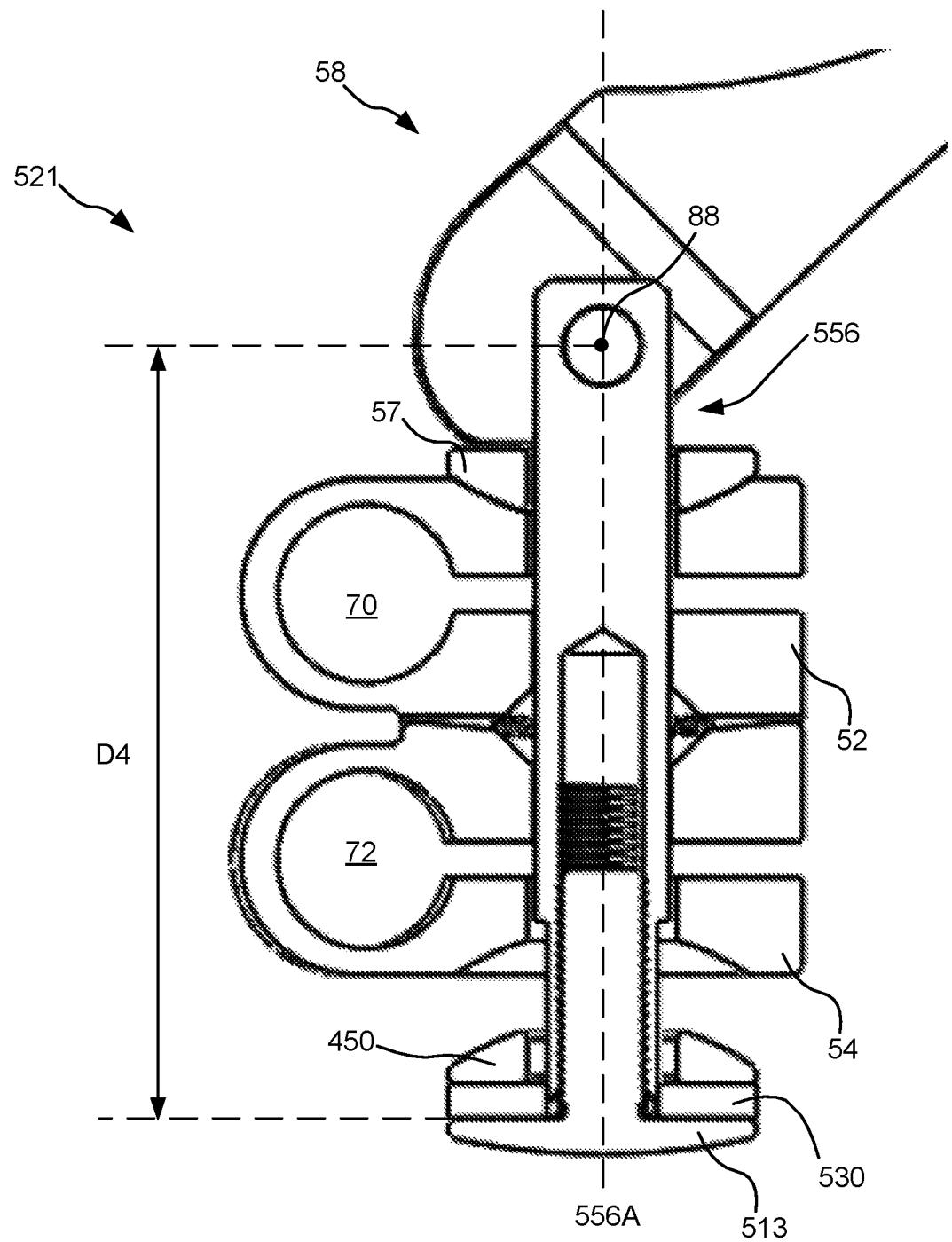
FIG. 20 shows a fifth embodiment of a joint clamp.
Figure 21:
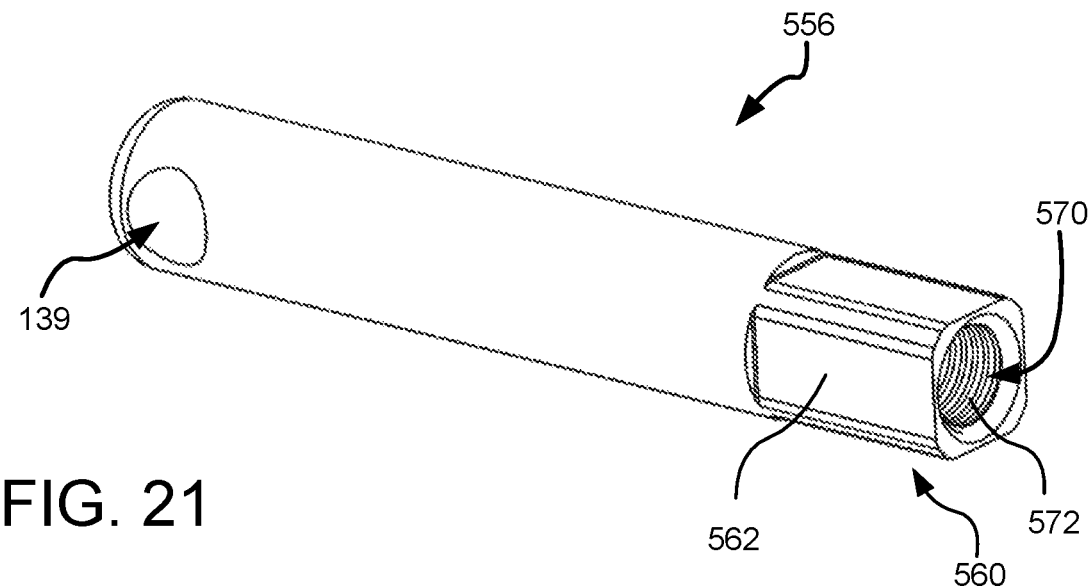
FIG. 21 provides a perspective view of the cam bolt for the joint clamp of FIG. 20.
Figure 22:
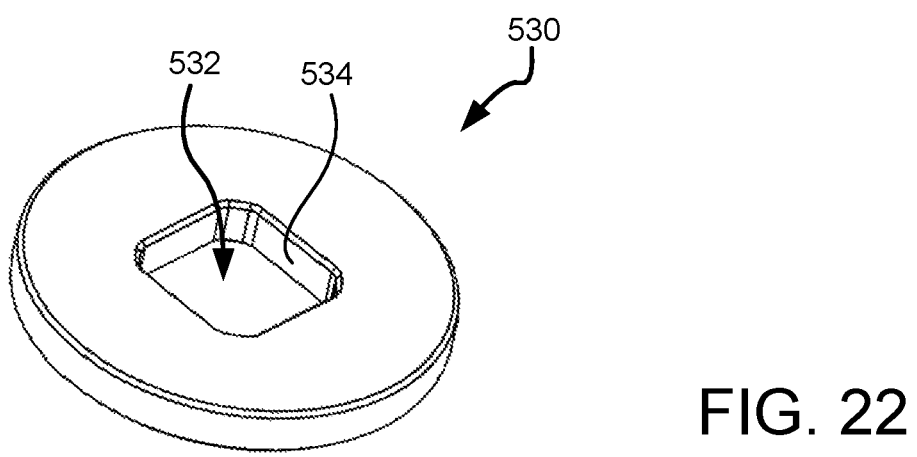
FIG. 22 provides a perspective view of a keyed washer for the joint clamp of FIG. 20.
Figure 23:
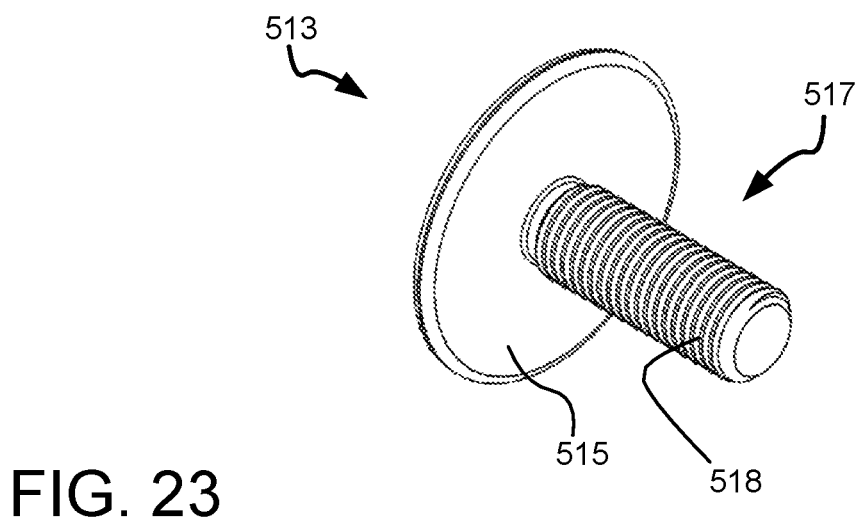
FIG. 23 provides a perspective view of a setting screw for the joint clamp of FIG. 20.
Figure 24:
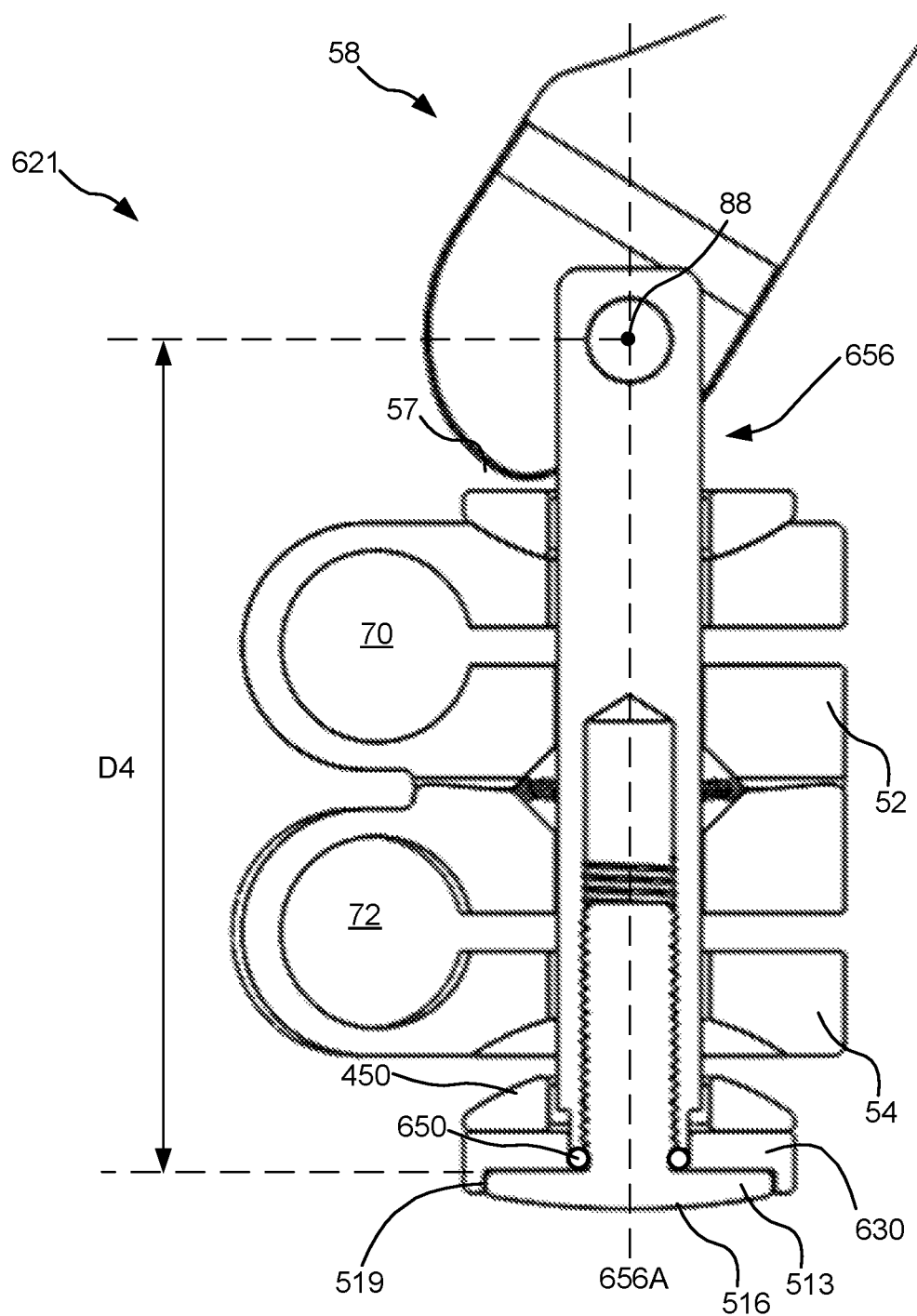
FIG. 24 shows a sixth embodiment of a joint clamp.

A fourth embodiment of a joint clamp is shown in FIGS. 17-19. The joint clamp 421 of FIGS. 17-19 may be implemented in a manner similar to the joint clamp 321 of FIG. 16. However, among other differences, the joint clamp 421 uses a cam bolt 456 with an adjustable length. Increasing the length of the cam bolt 456 increases a distance D3 between a pivot axis 88 and an upper surface of head 490, which decreases the pressure load placed on the clamps 52, 54 by the cam lever 58 when in a clamping position. Conversely, decreasing the length of the cam bolt 456 decreases the distance D3, which increases the pressure load placed on the clamps 52, 54. Thus, a desired clamping force may be obtained by adjusting the length of the cam bolt 456.

The cam bolt 456 includes an upper shaft 440 and a lower shaft 470 that engages the upper shaft 440. The lower shaft 470 may include an integral or fixed head 490 in a manner similar to the fixed head 390 of FIG. 16. The head 490 may engage a conical washer 450 with a conical upper surface similar to the conical upper surface 119 of nut 113. The lower shaft 470 may further include an internally-threaded bore 472 in its upper end 471. The bore 472 generally extends longitudinally into the lower shaft 470. Moreover, the bore 472 is sized to receive a lower end 441 of the upper shaft 440 and guide threads 442 of the upper shaft 440 into engagement with threads 474 along an inner surface of the bore 472.

Thus, the upper shaft 440 and the lower shaft 470 may engage each other to form the cam bolt 456. Moreover, rotation of the lower shaft 470 with respect to the upper shaft 440 may adjust the overall length of the cam bolt 456. In particular, rotation in a first direction (e.g. clockwise) may draw the upper shaft 440 into the internally-threaded bore 472 of the lower shaft 470 and decrease the length of the cam bolt 456. Conversely, rotation in an opposite second direction (e.g., counter-clockwise) may draw the upper shaft 440 from the internally-threaded bore 472 of the lower shaft 470 and increase the length of the cam bolt 456.

As further shown, the upper shaft 440 includes a keyed outer surface 446 near its lower end 441 and the lower shaft 470 includes a keyed outer surface 476 near its upper end 471. After the cam bolt 456 is set to a desired length, a sleeve 480 may be slipped over the keyed outer surfaces 446, 476. In particular, the sleeve 480 may include a keyed bore 482 that passes longitudinally through the sleeve 480. The cam bolt 456 may pass through the sleeve 480 via the keyed bore 482 and align keyed outer surfaces 446, 476 of the cam bolt 456 with internal surfaces of the keyed bore 482. The internal surfaces of the keyed bore 482 may closely mate and engage with the keyed outer surface 446, 476 of the cam bolt 456. When engaged, the keyed bore 482 may prevent rotation of the lower shaft portion 470 with respect to the upper shaft portion 440 and lock the cam bolt 456 to the desired length.

In one embodiment, the keyed outer surfaces 446, 476 each have twelve (12) sides or flats that circumscribe the shafts 440, 470. Similarly, the keyed bore 482 of the sleeve 480 has twelve (12) sides or flats that circumscribe its interior surface so as to engage and closely mate with the twelve (12) flats of the shafts 440, 470. Given twelve flats, the keyed outer surfaces 446, 476 and keyed bore 482 permit the upper shaft 440 to be aligned with the lower shaft 470 in 30° increments. Further, the threads 444, 474 have a thread count of 24 threads per inch, thus providing a length adjustment of ¹⁄₂₄" (0.04167") per full rotation or ¹⁄₂₈₈" (0.003472") per 30° increment. If finer adjustments to the length of the cam bolt 456 are desired, the number of flats (24, 36, etc.) and/or the thread count may be increased (e.g., 28, 30, etc.) to achieve a finer adjustment increment. Conversely, the number of flats and/or the thread count may be decreased to achieve a coarser adjustment increment.

The cam bolt 456 may further include an annular rib 483. The annular rib 483 may provide a surface or stop against which the sleeve 480 may rest. In one embodiment, the annular rib 483 is positioned below the keyed outer surface 476 of the lower shaft 470 such that the annular rib 483 positions the keyed bore 482 about the keyed outer surfaces 476, 496 when a lower surface 481 of the sleeve 480 engages the annular rib 483. For such an embodiment, the sleeve 480 may be slid over an upper end 448 of the upper shaft 440 and down to the annular rib 483 in order to position the keyed bore 482 of the sleeve 480 in engagement with the keyed outer surfaces 446, 476 of the cam bolt 456.

The joint clamp 421 may also include a tapered bushing 486. The tapered bushing 486 may include a cylindrical inner bore 487 that receives the sleeve 480 and closely mates with a cylindrical outer surface 485 of the sleeve 480. The tapered bushing 486 may further include an tapered outer surface in which a radius of a central portion of the bushing 486 is greater than the radii at upper and lower ends of the bushing 486. The tapered outer surface 489 may closely mate with an inner surface of apertures 112, 116 in clamps 52, 54 so as to position the tapered bushing 486 appropriately within the apertures 112, 116. As such, the sleeve 480 may rotate within and/or slide along the cylindrical inner bore 487 of the tapered bushing 486 while the keyed bore 482 of the sleeve 480 prevents the upper shaft 440 from rotating with respect to the lower shaft 470.

The sleeve 480 and the tapered bushing 486 are depicted as separate components. However, in some embodiments, the sleeve 480 and tapered bushing 486 may be implemented as a single component in which the sleeve 480 is essentially integrated with the bushing 486. In such embodiments, the tapered bushing 486 may include keyed bore 482 instead of the cylindrical inner bore 487. In such an embodiment, the tapered bushing 486 may directly engage outer surfaces 446, 476 of the upper shaft 440 and the lower shaft 470 without a separate, intervening sleeve.

As described above, the upper end 471 of the lower shaft 470 includes the bore 472 that receives the lower end 441 of the upper shaft 440. However, in some embodiments, the configuration may be reversed with the lower end 441 of the upper shaft 440 including an internally-threaded bore that receives an externally-threaded upper end 471 of the lower shaft 470.

A fifth embodiment of a joint clamp is shown in FIGS. 20-23. The joint clamp 521 of FIGS. 20-23 may be implemented in a manner similar to the joint clamp 21 of FIGS. 3-14. However, among other differences, the nut 113 of joint clamp 21 has been replaced with a setting screw 513, a washer 450, and a keyed washer 530. Moreover, the cam bolt 56 of the joint clamp 21 has been replaced with a keyed cam bolt 556.

As noted above with regard to joint clamp 421, the washer 450 has a conical upper surface that mates with the conically shaped aperture of the clamp 54. The keyed cam bolt 556 includes a keyed lower end 560 and a bore 570 that extends longitudinally into the lower end 560 of the cam bolt 556. The lower end 560 of the keyed cam bolt 556 includes an outer surface 562 with a cross-section that is square-shaped with chamfered corners. The keyed washer 530 likewise includes a keyed aperture 532 with a inner surface 534 with a cross-section that is square-shaped with chamfered corners.

The keyed lower end 560 and the keyed aperture 532 are sized such that the outer surface 562 of keyed cam bolt 556 closely mates with the inner surface 534 of the keyed washer 530 when the lower end 560 of the cam bolt 556 is received by the keyed aperture 532. Such engagement of the keyed cam bolt 556 with the keyed washer 530 essentially locks the washer 530 to the cam bolt 556. In particular, the keyed engagement ensures that the washer 530 rotates in unison with the cam bolt 556 about its longitudinal axis 556A.

The keyed lower end 560 further includes the bore 570. The bore 570 generally extends longitudinally into the keyed cam bolt 556. The bore 570 is sized to receive a shaft 517 of the setting screw 513. The bore 570 further includes threads 572 along an inner surface of the bore 570.

The setting screw 513 includes a head 515 and a shaft 517 that extends from head 515. The shaft 517 include threads 518 which engage threads 572 along an inner surface of the bore 570. In particular, the shaft 517 may pass through aperture 532 of the keyed washer 530, through the aperture of washer 450, and into internally-threaded bore 570 of the keyed cam bolt 556. Due to the engagement of threads 517, 572, tightening the setting screw 513 draws the setting screw 513 into the bore 566 and decreases a distance D4 between pivot axis 88 and an upper surface of the setting screw 513, which increases a clamping force of the joint clamp 521. Conversely, loosening the setting screw 513 draws the setting screw 513 from the bore 566 and increases the distance D4 between the pivot axis 88 and the upper surface of the setting screw 513, which decreases a clamping force of the joint clamp 521.

The thickness of the washer 530 or depth of the keyed aperture 532 establishes the range of adjustment provided by the setting screw 513. In particular, the setting screw 513 may be tightened (e.g., rotated in a first direction) until the lower end 560 of the keyed cam bolt 556 is drawn flush against the head 515 of the setting screw 513. For a proper setting, the keyed lower end 560 remains at least partially within the keyed aperture 532. Thus, the setting screw 513 may be loosened (e.g., rotated in a second direction opposite the first direction) until just before the lower end 560 of the keyed cam bolt 556 is drawn completely from the keyed aperture 532.

While the thickness of the washer 530 may limit the range of adjustment, unlike the joint clamp 421 which provides incremental adjustment, the setting screw 513 provides continuous adjustments within the range. As such, the joint clamp 521 may provide finer adjustments than the joint clamp 421.

In some embodiments, the setting screw 513 may be further affixed to the cam bolt 556 and the keyed washer 530 to further ensure the setting screw 513 does not rotate with respect to the cam bolt 556 after the setting screw 513 has been placed at the desired setting. For example, an epoxy, adhesive, solder, and/or other affixing material may be applied to the threads 517, 572. After such affixing material dries, cures, sets, etc., the affixing material may affix the setting screw 513 to the cam bolt 556 and help prevent the setting screw 513 from rotating with respect to the cam bolt 556.

The setting screw 513 may be further affixed to the keyed washer 530. For example, after appropriately adjusting the clamping force via the setting screw 513, the setting screw 513 may be welded (e.g., tack welded) to keyed washer to lock the setting screw 513 in place. However, the setting screw 513 may be affixed via other affixing techniques such as applying affixing materials (e.g., epoxies, adhesives, solders) and/or using other welding techniques.

As noted above, the engagement of the cam bolt 556 with the keyed washer 530 ensures that the cam bolt 556 and keyed washer 530 rotated in unison. By affixing the setting screw 513 to the keyed washer 530, the cam bolt, 556, keyed washer 530, and setting screw 513 likewise rotate in union. In this manner, a rotating cam bolt 556 and keyed washer 530 may be prevented from applying torque to the setting screw 513 that could otherwise tighten or loosen the setting screw 513 with respect to the cam bolt 556.

As another benefit, affixing the setting screw 513 to the keyed washer 530 also prevents the keyed washer 530 from sliding up and down the cam bolt 556 due to movement of the cam lever 58. Over time, such movement may introduce wear and degrade the keyed engagement between the cam bolt 556 with the keyed washer 530.

A sixth embodiment of a joint clamp is shown in FIGS. 24-28. The joint clamp 621 of FIGS. 24-28 may be implemented in a manner similar to the joint clamp 521 of FIGS. 20-23. However, among other differences, the keyed washer 530 of the joint clamp 521 has been replaced with a keyed washer 630 having a recess 640.

Similar to the joint clamp 521, the joint clamp 621 includes a keyed cam bolt 656 having a keyed lower end 660 and a bore 670 that extends longitudinally into the lower end 660 of the cam bolt 656. The lower end 660 of the keyed cam bolt 666 may have an outer surface 662 with a cross-section that is square-shaped with chamfered corners. The keyed washer 630 may likewise have a keyed aperture 632 with a inner surface 634 with a cross-section that is square-shaped with chamfered corners.

However, unlike the keyed washer 530, the keyed aperture 632 of keyed washer 630 does not extend completely through the keyed washer 630. As shown in FIG. 26, the keyed washer 630 includes a seat 635 with a circular aperture 636. The aperture 636 is sized to permit passage of the shaft 517 of the setting screw 513 through the keyed washer 630. The seat 635 provides a surface upon which a spring 650 rests. The spring 650 generally prevents the keyed washer 630 from sliding down the keyed cam bolt 656 when the clamping force is reduced, for example due to movement of the cam lever 58. In some embodiments, the spring 650 comprises a canted spring coil, which are available from various vendors such as Bal Seal Engineering. Other embodiments may use other types of springs for spring 650.

The keyed lower end 660 and the keyed aperture 632 are sized such that the outer surface 662 of keyed cam bolt 656 closely mates with the inner surface 634 of the keyed washer 630 when the lower end 660 of the cam bolt 656 is received by the keyed aperture 632. Such engagement of the keyed cam bolt 656 with the keyed washer 630 essentially locks the washer 630 to the cam bolt 656. In particular, the keyed engagement ensures that the washer 630 rotates in unison with the cam bolt 656 about its longitudinal axis 656A.

The keyed lower end 660 further includes the bore 670. The bore 670 generally extends longitudinally into the keyed cam bolt 656. The bore 670 is sized to receive a shaft 517 of the setting screw 513. The bore 672 further includes threads 672 along an inner surface of the bore 670.

The setting screw 513 includes a head 515 and a shaft 517 that extends from head 515. The shaft 517 includes threads 518 which engage threads 672 along an inner surface of the bore 670. In particular, the shaft 517 may pass through apertures 632, 636 of the keyed washer 630, through aperture of washer 450, and into internally-threaded bore 670 of the keyed cam bolt 656. Moreover, the recess 637 of the keyed washer 630 may receive the head 515.

In some embodiments, a depth of the recess 637 is greater than the thickness of the head 515. In such embodiments, the head 515 of the setting screw 513 does not extend beyond the washer 630, thus preventing unauthorized personnel from rotating the setting screw 513 with respect to the cam bolt 656 after assembly. In some embodiments, a depth of the recess 637 is greater than or nearly greater than a side wall thickness of the head 515. In such embodiments, an upper surface 516 of the head 515 may extend beyond the washer 630, but the washer 630 may cover of substantially cover the side walls 519 of the head 515. By covering or substantially covering the side walls 519, unauthorized personnel may be unable to rotate the setting screw 513 with respect to the cam bolt 656 after assembly. In this manner the recessed washer 630 may prevent tampering or inadvertent adjustment of the setting screw 513 after calibration and assembly.

Similar to other embodiments, due to the engagement of threads 518, 672, tightening the setting screw 513 draws the setting screw 513 into the bore 670 and increases a clamping force of the joint clamp 621. Conversely, loosening the setting screw 513 draws the setting screw 513 from the bore 670 and decreases a clamping force of the joint clamp 621.

In some embodiment, the setting screw 513 may be further affixed to the cam bolt 656 and/or the keyed washer 630 to further ensure the setting screw 513 does not rotate with respect to the cam bolt 656 after the setting screw 513 has been placed at the desired setting. For example, an epoxy, adhesive, and/or other affixing material may be applied to the threads 518, 672. After such affixing material dries, cures, sets, etc., the affixing material may affix the setting screw 513 to the cam bolt 656 and help prevent the setting screw 513 from rotating with respect to the cam bolt 656.

Furthermore, the setting screw 513 may be affixed to the keyed washer 630. For example, after appropriately adjusting the clamping force via the setting screw 513, the setting screw 513 may be welded (e.g., tack welded) to keyed washer 630 to lock the setting screw 513 in place. However, the setting screw 513 may be affixed via other techniques such as applying affixing materials (e.g., epoxies, adhesives, solders, etc.) and/or using other welding techniques.

As noted above, the engagement of the cam bolt 656 with the keyed washer 630 ensures that the cam bolt 656 and keyed washer 630 rotated in unison. By affixing the setting screw 513 to the keyed washer 630, the cam bolt 656, keyed washer 630, and setting screw 513 likewise rotate in union. In this manner, a rotating cam bolt 656 and keyed washer 630 may be prevented from applying torque to the setting screw 513 that could otherwise tighten or loosen the setting screw 513 with respect to the cam bolt 656.

While particular embodiments of the invention have been shown, it will be understood that the invention is not limited thereto since modifications may be made by those skilled in the art, particularly in light of the foregoing teaching. For example, the multi-directional joint clamps have been described with a stack of two clamps. However, the various described embodiments of the multi-directional joint clamps may be implemented with two, three, or more stacked clamps. It is, therefore, the appended claims which define the true spirit and scope of the invention.

What is claimed is:

1. A joint clamp for use in a surgical retractor system, the joint clamp comprising:
   clamps, each clamp comprising a passage having a perimeter that is adjusted by a clamping force applied to an upper surface and a lower surface of the respective clamp;
   a cam bolt that passes through the clamps, the cam bolt comprising an upper shaft and a lower shaft rotatably engaged with the upper shaft, wherein rotation of the lower shaft with respect to the upper shaft adjusts a length of the cam bolt; and
   a cam lever comprising a cam head pivotally attached to the upper shaft of the cam bolt to permit rotation about a pivot axis that is perpendicular to a longitudinal axis of the cam bolt, the cam head having an outer surface that results in a distance between the pivot axis and an upper surface of the clamps being greater when the cam lever is rotated about the pivot axis to a clamping position than when the cam lever is rotated about the pivot axis to a non-clamping position.

2. The joint clamp of claim 1, further comprising a washer between a head of the lower shaft and a lower surface of the clamps.

3. The joint clamp of claim 1, wherein rotation of the upper shaft with respect to lower shaft adjusts a distance between the pivot axis and a head of the lower shaft.

4. The joint clamp of claim 1, further comprising a sleeve with a keyed inner surface that engages keyed outer surfaces of the upper shaft and the lower shaft and prevent rotation of the upper shaft with respect to the lower shaft.

5. The joint clamp of claim 4, further comprising a bushing comprising a bore, wherein an inner surface of the bore engages an outer surface of the sleeve.

6. The joint clamp of claim 5, wherein:
   the cam bolt further comprises an annular rib; and
   an outer surface of the bushing engages the annular rib.

7. The joint clamp of claim 1, further comprising a tapered bushing with a keyed inner surface that engages keyed outer surfaces of the upper shaft and the lower shaft and prevent rotation of the upper shaft with respect to the lower shaft.

8. The joint clamp of claim 1, wherein the lower shaft comprises an externally threaded portion received by an internally threaded bore of the upper shaft.

9. The joint clamp of claim 1, wherein the upper shaft comprises an externally threaded portion received by an internally threaded bore of the lower shaft.

10. A joint clamp for use in a surgical retractor system, the joint clamp comprising:
    clamps, each clamp comprising a passage having a perimeter that is adjusted by a clamping force applied to the respective clamp;
    a cam bolt assembly that passes through the clamps, the cam bolt assembly comprising a cam bolt upper subassembly and a cam bolt lower subassembly, wherein rotation of a member of the cam bolt lower subassembly with respect to the cam bolt upper subassembly adjusts a length of the cam bolt assembly; and
    a cam lever comprising a cam head pivotally attached to the cam bolt upper subassembly to permit rotation about a pivot axis that is perpendicular to a longitudinal axis of the cam bolt assembly, the cam head having an outer surface that results in a distance between the pivot axis and an upper surface of the clamps being greater when the cam lever is rotated about the pivot axis to a clamping position than when the cam lever is rotated about the pivot axis to a non-clamping position.

11. The joint clamp of claim 10, wherein:
the cam bolt upper subassembly comprises a cam bolt that passes through the clamps;
the member of the cam bolt lower subassembly comprises a screw; and
the screw comprises a threaded shaft that engages an internally threaded bore of the cam bolt.

12. The joint clamp of claim 11, wherein:
the cam bolt lower subassembly comprises a first washer;
the first washer comprises an aperture with a keyed inner surface; and
the cam bolt comprises a keyed outer surface that engages the keyed inner surface of the aperture.

13. The joint clamp of claim 12, wherein:
the first washer comprises a lower surface with a recess sized to receive a head of the screw; and
a depth of the recess is greater than a thickness of the head of the screw.

14. The joint clamp of claim 10, wherein:
the cam bolt upper subassembly comprises a cam bolt upper shaft; and
the member of the cam bolt lower subassembly comprises a cam bolt lower shaft rotatably engaged with the cam bolt upper shaft.

15. The joint clamp of claim 14, comprising a sleeve with a keyed inner surface that engages keyed outer surfaces of the cam bolt upper shaft and the cam bolt lower shaft and prevents rotation of the cam bolt upper shaft with respect to the cam bolt lower shaft.

16. The joint clamp of claim 15, comprising:
a bushing comprising a bore and tapered outer surfaces;
wherein an inner surface of the bore engages an outer surface of the sleeve; and
wherein the tapered outer surfaces of the bushing engage surfaces of the clamps.

17. The joint clamp of claim 16, wherein:
the cam bolt lower shaft comprises an annular rib; and
a lower surface of the sleeve rests on an upper surface of the annular rib.

18. The joint clamp of claim 14, wherein:
the cam bolt lower shaft comprises an externally threaded portion; and
the cam bolt upper shaft comprises an internally threaded bore that engages the externally threaded portion of the cam bolt lower shaft.

19. The joint clamp of claim 14, wherein:
the cam bolt upper shaft comprises an externally threaded portion; and
the cam bolt lower shaft comprises an internally threaded bore that engages the externally threaded portion of the cam bolt upper shaft.

20. The joint clamp of claim 10, wherein:
the clamps include a first clamp stacked on a second clamp; and
the first clamp and the second clamp are independently rotatable about an axis of the cam bolt.

\* \* \* \* \*